United States Patent [19]

Kraft et al.

[11] 4,099,007
[45] Jul. 4, 1978

[54] N,N-SUBSTITUTED 2,4,5-TRIKETOIMIDAZOLIDINES AND A PROCESS FOR THEIR PREPARATION

[75] Inventors: Kurt Kraft, Auringen; Johannes Reese, Wiesbaden-Biebrich, both of Germany

[73] Assignee: Hoechst Aktiengesellschaft, Wiesbaden, Germany

[21] Appl. No.: 586,035

[22] Filed: Jun. 11, 1975

Related U.S. Application Data

[60] Division of Ser. No. 230,989, Mar. 1, 1972, Pat. No. 3,928,376, which is a continuation-in-part of Ser. No. 24,794, Apr. 1, 1970, abandoned.

[30] Foreign Application Priority Data

Apr. 2, 1975 [DE] Fed. Rep. of Germany ....... 1916932
Apr. 24, 1975 [DE] Fed. Rep. of Germany ....... 1920845

[51] Int. Cl.² .................. C07D 233/96; C08G 18/06; C08G 18/14
[52] U.S. Cl. .............................. 548/307; 260/45.8 N; 260/287 R; 260/295 D; 260/304 R; 260/305
[58] Field of Search ................ 260/309.5, 77.5 CH, 260/45.8 N; 528/307

[56] References Cited

U.S. PATENT DOCUMENTS

| | | | |
|---|---|---|---|
| 3,609,113 | 9/1971 | Schade et al. | 260/309.5 |
| 3,661,859 | 5/1972 | Patton | 260/77.5 CH |
| 3,928,376 | 12/1975 | Reese et al. | 260/309.5 |

OTHER PUBLICATIONS

Patton, Jour. Org. Chem., vol. 32, pp. 383–388, (1967).
Biltz et al. (I), Chem. Abs. 1913, vol. 7, pp. 2574–2575.
Biltz et al. (II) Berichte 1913, vol. 46 pp. 1387–1404.
Stieger, Chem. Abs. 1917, vol. 11, pp. 1137–1138.
DOS 1916932, Reichhold-Albert Chem. A/G (Kraft & Reese) Oct. 5, 1970.

*Primary Examiner*—H.S. Cockeram
*Attorney, Agent, or Firm*—Littlepage, Quaintance, Richardson, Murphy and Webner

[57] ABSTRACT

A process for the preparation of a monomer compound containing a structural unit of the formula

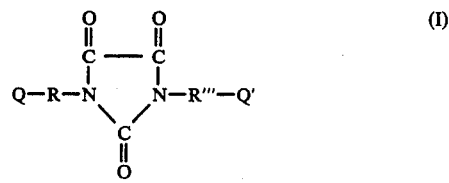

wherein one of Q and Q' are independently the group —NH—CO—OR$^{IV}$ or hydrogen and the other —NH—CO—COOR$^V$ or hydrogen, a urethane or an isocyanate, wherein R$^{IV}$ and R$^V$ aliphatic or carbocyclic hydrocarbon groups being substituted or unsubstituted group; R and R''' are unsubstituted or monosubstituted aromatic radicals (wherein at least one oxamidic ester and) wherein at least one oxamidic acid ester with the grouping —NH—CO—CO—OR$^V$, wherein R$^V$ is as defined, is reacted with an isocyanate or an isocyanate forming compound at temperatures of −20° to +280° C in the presence or absence of a catalyst,
a compound of said formula and a shaped article containing said compound.

4 Claims, No Drawings

N,N-SUBSTITUTED 2,4,5-TRIKETOIMIDAZOLIDINES AND A PROCESS FOR THEIR PREPARATION

This application is a divisional application of application Ser. No. 230,989 filed in Mar. 1, 1972 now U.S. Pat. No. 3,928,376 which is a continuation-in-part application Ser. No. 24,794 filed in Apr. 1, 1970, abandoned.

The invention relates to N,N'-substituted 2,4,5-triketoimidazolidines.

It has been proposed to obtain 2,4,5-triketoimidazolidines of formula

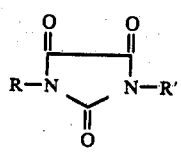

in which -R and -R' are the same or different and are selected from aromatic, cycloaliphatic and aliphatic groups, either of which may also be substituted, according to the following processes:

(1) By reaction of N,N'-disubstituted ureas with oxalyl chloride:

R—NH—CO—NH—R' + Cl—CO—COCl $\xrightarrow{-2 \text{ HCl}}$

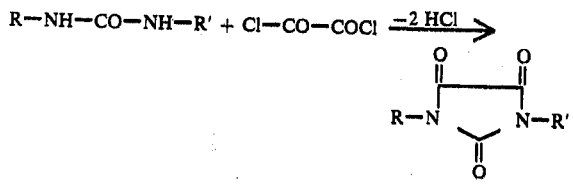

(2) By reaction of N,N'-substituted ureas with ethoxalyl chloride:

R—NH—CO—NH—R' + Cl—CO—CO—OC$_2$H$_5$ $\xrightarrow[-C_2H_5OH]{-HCl}$

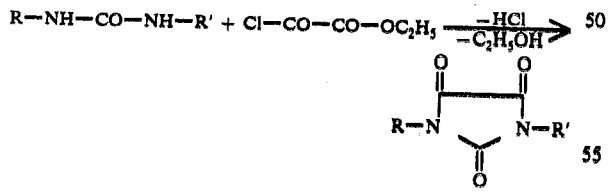

(3) By reaction of N,N'-substituted ureas with dialkyl oxalates:

R-NH-CO-NH-R' + alkyl-O-CO-CO-O-alkyl $\xrightarrow{-2 \text{ alkanol}}$

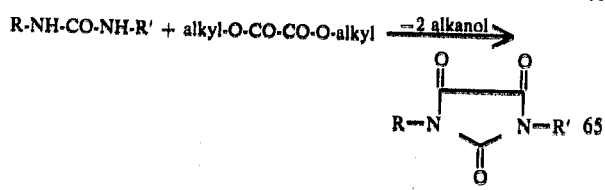

In addition, there are a number of complicated syntheses which start from substituted thioureas. They have not acquired any importance.

The reaction according to 1) requires oxalyl chloride which is expensive and due to its sensitivity to hydrolysis, difficult to handle.

In addition, the ureas to be used as reaction components have to be synthesised. This neccesitates purification operations particularly with asymmetrically substituted types, in order to remove by-products.

The reaction according to 2) requires ethoxalyl chloride which is likewies expensive and can only be prepared from oxalyl chloride. Otherwise the statements made about reaction 1) also apply here.

The reaction according to 3) would as such be a convenient method but due to the low reactivity of the esters it only succeeds in a few cases. The yields are low and the reaction times extremely long.

A further disadvantage is common to all three methods; in many cases the ureas used as starting materials are sparingly soluble compounds which, after an incomplete reaction to form the 2,4,5-triketoimidazolidines, can only be separated therefrom with difficulty.

Now according to the invention there are provided compounds of general formula

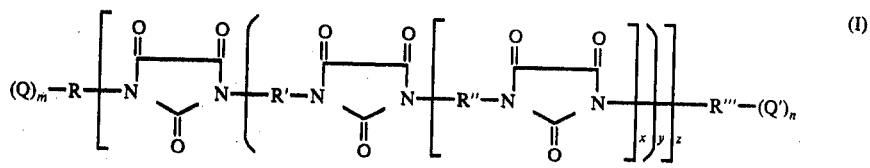

wherein one of Q,Q' is the group —NH—CO—OR$^{IV}$ and the other —NH—CO—COOR$^V$, a urethane or and isocyanate group, wherein R$^{IV}$ and R$^V$ are aliphatic hydrocarbon groups with up to 18 carbon atoms, cycloaliphatic hydrocarbon groups with up to 8 carbon atoms, mononuclear aromatic hydrocarbon groups with 6 carbon atoms, or such mononuclear aromatic groups of 6 carbon atoms substituted with hydrocarbon groups having up to 14 carbon atoms and $m$ and $n$ each are independently zero or 1.

R is (a) mono- or polynuclear mono- to hexavalent unsubstituted aromatic radical having up to 14 carbon atoms wherein a mononuclear radical is only present in a compound of formula (I) having more than one triketoimidazolidine ring;

(b) a mono- or polynuclear mono- to hexavalent aromatic radical having up to 20 carbon atoms being substituted by at least one substituent selected from halogen, nitro, cyano, dialkylamino, diarylamino, alkylarylamino, alkyl, haloalkyl, alkylsulphonyl, alkoxy, alkylester, arylester, acyl, and cycloalkyl groups having up to 18 carbon atoms, a ($\omega - m$) ketoalkyl radical having up to 5 carbon atoms, wherein the substitution by at least one halogen atom or at least one alkyl radical in a mononuclear aromatic radical is present only in a compound b1) having more than one triketoimidazolidine ring or b2) in a compound having at least one substituent of the group alkoxy, alkylester, alkylsulphonyl, nitro, and CF$_3$;

(c) a mono- to hexavalent unsubstituted heteroaromatic radical selected from the group benzothiazolyl, phenyl, thiophenyl, benzofuryl, N-methylcarbazolyl, quinolyl, pyridyl, quinonyl;

(d) a mono- to hexavalent substituted heteroaromatic radical having up to 20 carbon atoms selected from the group benzothiazolyl, phenyl, thiophenyl, benzofuryl, N-methylcarbazolyl, quinolyl, quinonyl, pyridyl being substituted by at least one substituent selected from halogen, nitro, cyano, dialkylamino, diarylamino, alkylarylamino, alkyl, haloalkyl, alkylsulphonyl, alkoxy, alkylester, arylester, acyl, and cycloalkyl groups having up to 18 carbon atoms, a ($\omega - m$) ketoalkyl radical having up to 5 carbon atoms;

wherein at least one nucleus of said aromatic nuclei may be quinoid and wherein polynuclear aromatic groups may be linked by aliphatic groups or by hetero atoms; and wherein the aromatic part of the radicals b) to d) is directly bound to the triketoimidazolidine nucleus and wherein in a compound of the formula (I) having only one triketoimidazolidine ring R is not phenyl or a halogen substitution product thereof if R''' is phenylene or a halogenated phenylene group or hydrogen.

R' is (e) a group as defined for R wherein R' may also be a mononuclear radical as defined under a) and b) in compounds having only one triketoimidazolidine nucleus;

(f) a saturated aliphatic hydrocarbon radical having up to 18 carbon atoms, (g) a cycloaliphatic unsubstituted hydrocarbon radical having up to 12 carbon atoms, (h) a substituted cycloaliphatic hydrocarbon radical having 1 to 6 substituents and having up to 20 carbon atoms;

R'' is a group as defined for R;
R''' is a group as defined for R' and at most tetravalent;
$x$ = zero or 1 if $y$ = 1.
$y$ = zero or an integer from 1 to 70;
$z$ = an integer from 1 to 6;
with the provisos that one of the groups R and R'' is aromatic and if R''' is aliphatic or cycloaliphatic, the group R, R' and R'' adjacent to R''' is aromatic, and that R and R''' have a meaning other than phenyl if $m$, $n$, and $y$ all equal zero.

$R^{IV}$ and $R^{V}$ are preferably aliphatic hydrocarbon groups with up to 6 carbon atoms, e.g. alkyl groups, phenyl groups or phenyl groups substituted with alkyl groups having up to 6 carbon atoms.

In formula (I) R, R', and R''' may be the same or different; $z$ is preferably 1 to 3 and is at least 2 if $m$ = zero.

These compounds may be prepared without the abovestated difficulties.

The compounds according to the invention corresponding to formula (I) can thus also be branched if R is branched. It is furthermore possible for the compounds to comprise only one triketoimidazolidine ring. This is the case if $x$ and $y$ are zero in the above formula. One then obtains compounds of formula

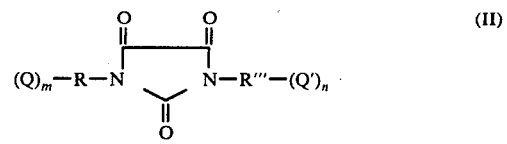

wherein preferably

R is a polynuclear cyclic, preferably aromatic group with up to 14 carbon atoms in the ring system, which group may be substituted e.g. by acetyl and wherein each nucleus can carry one to four or — if $m$ is zero - up to five substituents, or a mononuclear cyclic group with up to 14 carbon atoms, with the proviso that R is not phenyl or the halogenation substitution products thereof if R''' is a phenylene or halogenphenylene group or hydrogen;

R''' is a hydrocarbon ring with up to 20 carbon atoms, which may carry one to six and — if $n$ is zero — up to five substituents in a ring and which is e.g. aromatic, straight chained or branched aliphatic or cycloaliphatic, and wherein Q and Q', $m$ and $n$ have the above-stated meaning. Suitable R-groups in the compound according to formula II are, for example, phenyl, naphthyl, benzeneazophenyl, benzothiazolyphenyl, anthraquinonyl, pyridyl or cycloaliphatic groups, each of which can be substituted with one or more groups selected from alkyl, cycloalkyl or haloalkyl groups with up to 5 halogen atoms, alkoxy, acyl, aroyl, cycloalkyl or ester groups with up to 20 carbon atoms, alkyl or arylsulphonyl groups each with up to 15 carbon atoms, halogen atoms, trifluormethyl, acyl, such as acetyl groups, nitro and cyano groups.

Suitable groups R''', in addition to the groups stated for R, are preferably phenyl or naphthyl or phenylene or naphthylene groups, each of which can be substituted with alkyl, haloalkyl with up to 5 halogen atoms, trifluormethyl, acyl such as acetyl, or nitro groups.

According to another feasible embodiment the compounds according to formula (I) can also be compounds of formula (III)

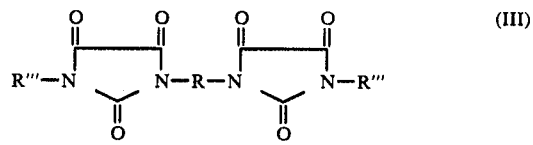

wherein R and R''' have the meaning stated for formula (I).

Other compounds according to the invention are illustrated, by way of example, by the following formulae:

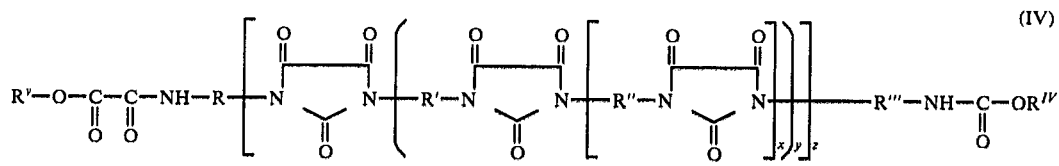

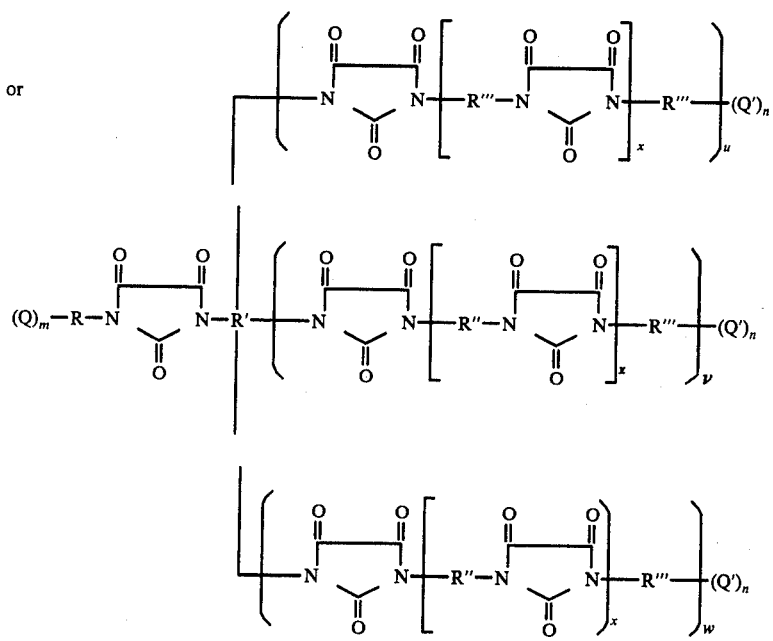

or

The compounds V can also be branched, the branching point being situated in group R'. Due to their polyfunctionality, also R, R', R" and R'" in the compounds of formula (I) can be branched.

In the compounds according to formula (V) R, R', R''', $R^{IV}$, $R^V$, Q, Q', m, n, x, y and z have the meanings defined above; u, v, and w can be independently zero or an integer from 1 to 70, at least one of u, v, and w being 1.

A further aspect of the invention provides a process for the preparation of a compound of general formula (I) wherein one of Q, Q' is the group —NH—CO—OR$^{IV}$ and the other —NH—CO—COOR$^V$, a urethane or an isocyanate group, wherein $R^{IV}$ and $R^V$ are aliphatic hydrocarbon groups with up to 18 carbon atoms, cycloaliphatic hydrocarbon groups with up to 8 carbon atoms, mononuclear aromatic hydrocarbon groups of 6 carbon atoms, or such mononuclear aromatic groups of 6 carbon atoms substituted with hydrocarbon groups having up to 14 carbon atoms, and m and n each are independently zero or 1.

R is (a) mono- or polynuclear mono- to hexavalent unsubstituted aromatic radical having up to 14 carbon atoms;

(b) a mono- or polynuclear mono- to hexavalent aromatic radical having up to 20 carbon atoms being substituted by at least one substituent selected from halogen, nitro, cyano, dialkylamino, diarylamino, alkylarylamino, alkyl, haloalkyl, alkylsulphonyl, alkoxy, alkylester, arylester, acyl, and cycloalkyl groups having up to 18 carbon atoms, a ($\omega - m$) ketoalkyl radical having up to 5 carbon atoms;

(c) a mono- to hexavalent unsubstituted heteroaromatic radical selected from the group benzothiazolyl, phenyl, thiophenyl, benzofuryl, N-methylcarbazolyl, quinolyl, pyridyl, quinonyl;

(d) a mono- to hexavalent substituted heteroaromatic radical having up to 20 carbon atoms selected from the group benzothiazolyl, phenyl, thiophenyl, benzofuryl, N-methylcarbazolyl, quinolyl, quinonyl, pyridyl being substituted by at least one substituent selected from halogen, nitro, cyano, dialkylamino, diarylamino, alkylarylamino, alkyl, haloalkyl, alkylsulphonyl, alkoxy, alkylester, arylester, acyl, and cycloalkyl groups having up to 18 carbon atoms, a ($\omega - m$) ketoalkyl radical having up to 5 carbon atoms;

wherein at least one nucleus of said aromatic nuclei may be quinoid and wherein polynuclear aromatic groups may be linked by aliphatic groups or by hetero atoms; and wherein the aromatic part of the radicals b) to d) is directly bound to the triketoimidazolidine nucleus;

R' is (e) a group as defined for R;

(f) a saturated aliphatic hydrocarbon radical hyving up to 18 carbon atoms;

(g) a cycloalphatic unsubstituted hydrocarbon radical having up to 12 carbon atoms;

(h) a substituted cycloaliphatic hydrocarbon radical having 1 to 6 substituents and having up to 20 carbon atoms;

R" is a group as defined for R;

R'" is a group as defined for R' and at most tetravalent;

x = zero or 1 if y = 1;

y = zero or an integer from 1 to 70;

z = an integer from 1 to 6;

with the provisos that one of the groups R and R" is aromatic and if R'" is aliphatic or cycloaliphatic, the group R, R' and R" adjacent to R'" is aromatic which comprises reacting at least one ester of oxamidic acid with the grouping —NH—CO—CO—OR$^V$, wherein $R^V$ is as defined with an isocyanate or an isocyanate-forming compound at temperatures of −20° to +280° C in the presence or absence of a catalyst.

In the compound obtained according to this process $R^V$ is preferably a hydrocarbon group and it may also be substituted by isocyanateforming groups. The triketoimidazolidines are thus obtained in high yields.

The reaction can be performed eg according to the following schemes (1a) and (1b):

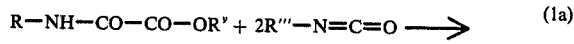

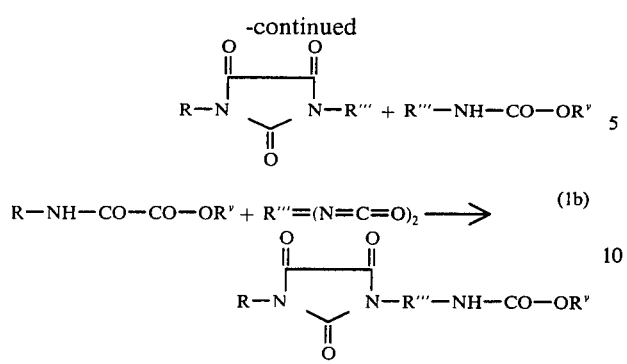

(1b)

wherein R R''' and $R^V$ have the meaning stated above.

In this reaction, a completely novel cyclisation is concerned in which one mol of the isocyanate serves as the condensation agent for splitting off the alcohol $R^V$—CH. The oxamidate esters used as starting material may be obtained in known manner by reacting mono- or di-amines with oxalate esters, e.g. dialkyl oxalates. The general formula (I) applies to products obtained according to scheme (1a).

Due to its excellent solubility, the carbamic acid derivative formed as a by-product can readily be separated in conventional solvents, such as ligroin, benzene, toluene ethanol, isopropanol, ether or tetrahydrofuran, from the 2,4,5-triketoimidazolidines which are mostly difficulty soluble in the above-stated solvents.

The process is equally suitable for the preparation of symmetrical, as well as asymmetrical triketoimdazolidines.

Oxamidate esters of formula

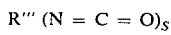 (VII)

wherein r is an integer from 1 to 6, and R and $R^V$ have the above meaning,
are preferably reacted with isocyanates of formula $$R''' (N = C = O)_s$$

wherein R''' has the above meaning and s is an integer from 1 to 4, to form compounds of the general formula (I), wherein R, R',R''', $R^V$, x and y have the above meaning but in which R and R''' can also be phenyl if m, n and y are zero, whereupon, if desired, the polymerisable groups formed are polymerised. As "polymerisation" there is to be understood a chain elongation by means of addition and/or condensation.

In this manner it is possible to prepare — also without polymerisation — monomeric compounds with up to three triketoimidazolidine groups. This is the case when starting e.g. from monoisocyanates and tris-oxamidate esters. In the preparation of these compounds, however, care should be taken that amino radicals in the cyclic group R are not disposed in the o-position. Further products of this reaction are compounds according to the above formulae IV and V.

When the starting material in the above reaction is a bisoxamidate ester of formula

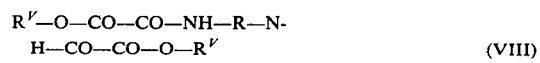 (VIII)

the novel bis-(2,4,5-triketoimidazolidines) of formula (III) are obtained in high yields according to the following scheme:

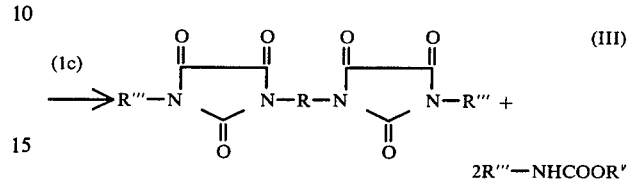

wherein R, R''' and $R^V$ have the above-defined meanings and the two substituents R''' are preferably the same but may be different. This can be the case if the oximidate esters are reacted with e.g. a mixture of isocyanates. Their synthesis according to the known processes 1) – 3) could only be performed with difficulty owing to the low solubility of the bis-ureas required.

In the reaction between the oxamidate esters and the isocyanates with subsequent polymerisation, products having a relatively low degree of polymerisation are obtained. In this reaction one mol of bis-oxamidate ester can react, for example, with one mol of diisocyanate analogously to scheme (1) only one isocyanate group being used, however, for the cyclisation, whilst the other assumes the role of the condensation agent, i.e. the alcohol liberated in the cyclisation, is intramoleculary incorporated into compound IX. This reaction takes place according to the scheme

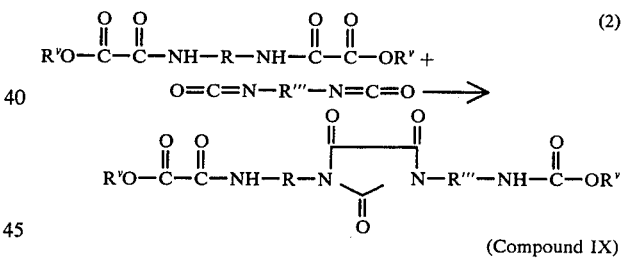

(Compound IX)

In addition, however, also multiple forms of compound IX can be formed:

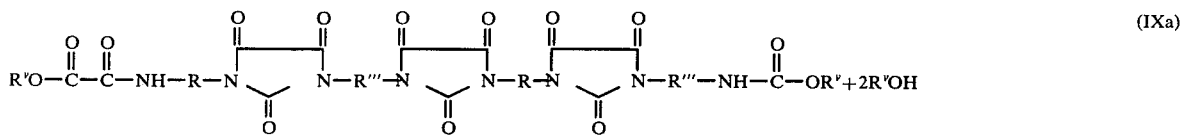

In these cases the alcohol liberated by the cyclisation can be taken up intramolecularly by the polymer and/or extramolecularly by the still unsaturated isocyanate.

Common to all the compounds are the end groups

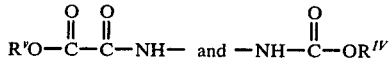

$R^{IV}$ and $R^V$ can be differnt when a mixture of oxamidate esters with different alkyl groups is used. Further, the reaction of bis-oxamidate esters with diisocyanates can theoretically be expected to take place, e.g. as follows:

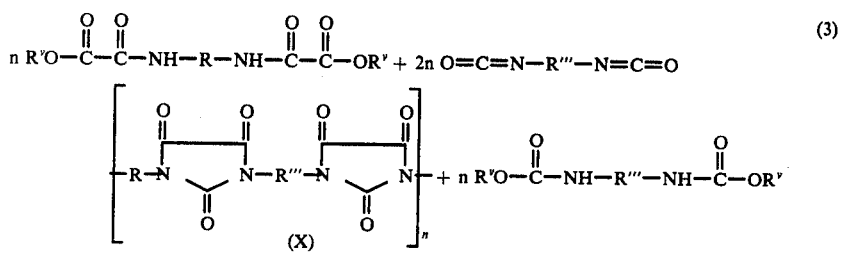
(3)

The IR-spectroscopic examination of the reaction products obtained according to the invention clearly proved the presence of —NHCOOR'-groups. In addition, there was also found the band grouping characteristic for the 2,4,5-triketoimidazoline ring

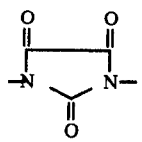

as a result of which the reaction according to formula scheme (2) is confirmed.

It is certain that in the process claimed, the polymers of scheme (3) are only formed in small quantities if the reaction conditions are chosen correctly. These polymers can indeed be recognised due to the fact that they are insoluble in the conventional solvents which contain no reactive protons ("aprotic solvents") e.g. dimethylformamide, N-methylpyrrolidone, dimethylsulphoxide, N,N',N''-hexamethylphosphoric acid triamide). The products obtained according to the process claimed are, however, readily soluble in such solvents. Even 30-60% solutions can be obtained without difficulty in the above-mentioned aprotic solvents without the viscosity of said solutions being very high. The solutions also remain unchanged during storage and they do not tend to crystallise. These properties facilitate an extended use of the products prepared according to the invention for obtaining heterocyclic polymeric products.

Specifically, if the monomeric compounds according to the invention, either in solution or free of solvent, are heated in the molten or solid state, at 120°-550° C preferably at 280°-450° C the end groups thereof react according to the following scheme (4) resulting in the formation of practically insoluble film-forming polymers which are resistant to chemical attack and remain unaffected by changes of temperature.

It is not necessary to use the reaction components in a mixture; in fact it is also possible to carry out the reaction so that first one component is introduced, if desired, in admixture with only a minor portion of the second component, and that the main quantity of the second component is then added. This method can be carried out either in solution or in the melt. The catalyst can in this case be added to the reaction component introduced first and/or to that used later.

If the reaction temperature is chosen so high, e.g. from 150° to 300° C, that the reaction of the end groups

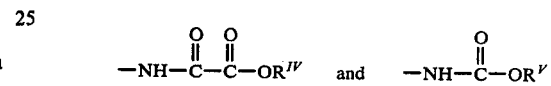

proceeds at a sufficient speed, polymers insoluble in the aforesaid aprotonic solvents can be obtained in many cases according to equ. (4). They can likewise be separated off by filtration. They take the form of pale yellow to brownish powders which are generally only soluble in hot concentrated sulphuric acid. They are separated, practically unchanged, from this solution by addition of e.g. water.

The compounds claimed are obtained as powders or as crystalline, e.g. also microcrystalline, substances.

In compounds IV and V the same groups as in compound II can form the end groups. In compound I it is also possible to have oxamidate ester groups on both sides or these ester groups on only one side, and either urethane or isocyanate groups on the other side, or urethane or isocyanate groups on both sides.

The reaction according to scheme (4) is a condensation, whilst reaction (3) is an addition followed by a condensation and reaction (2) is an addition.

As it is clearly apparent, the new process permits the reaction of entirely different starting materials. The products thereof may be used for an extremely large number of purposes.

The high chemical uniformity of the polymers obtained is shown by the outstanding ability to form films and foils. The thermal stability is particularly high in (4)
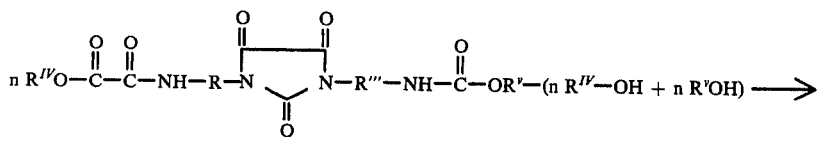
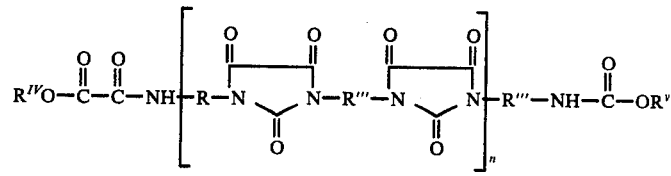

products having a low hydrogen content, especially however, in the absence of aliphatically or cycloaliphatically bonded hydrogen in the heterocyclic system. The films and foils which are obtained from the above intermediates are further distinguished by very good elasticity properties.

The R-group in the oxamidate esters is of an aromatic nature, i.e. a carbocyclic or heterocyclic group, preferably with an aromatic character. It can be e.g. phenyl, naphthyl, benzeneazophenyl, benzothiazolylphenyl, anthraquinonyl or pyridyl.

Suitable bifunctional groups R of the bis-oxamidate esters are e.g.

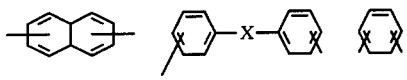

wherein X is —CH$_2$—, —O—, —S—, S—S—, —SO$_2$—, —N=N—, NR$^{VII}$—, (—R$^{VII}$ is here an aliphatic, cycloaliphatic or aromatic group with up to 8 carbon atoms), or R may be diphenylene, dimethyldiphenylene, anthraquinonylene, pyridylene, quinonylene, quinolylene, thiophenylene, benzofurylene, and N-methylcarbazolylene groups. The group R— can furthermore carry one or more substituents in one or more aromatic and/or heterocyclic nuclei or in the side chain, so long as the substituents do not react with the isocyanates under the conditions of reaction employed. These substituents can be alkyl, alkoxy, haloalkyl, ester, alkylketo, (ω — m) - ketoalkyl, or alkylsulphonyl groups, each with 5 C — atoms, wherein $m$ is an integer from 1 to 3, such as —CH$_3$, —C$_2$H$_5$, —OCH$_3$, —OC$_2$H$_5$, CF$_3$, —COOHC$_2$H$_5$, —CN, —COCH$_3$, —SO$_2$CH$_3$; the substituents may be nitro or cyano groups or halogen, especially F, Cl, Br. In a similar manner also tris and/or tetrakis — oxamidate esters can be used by themselves alone or in mixture with the bis-oxamidate esters.

The group R′′′ in the isocyanates is mono- to tetravalent, e.g. an aliphatic, cycloaliphatic, aromatic or mixed aromatic-aliphatic group with up to 20, preferably up to 15 C-atoms, e.g. cyclohexyl, butyl, octyl, octadecyl, or

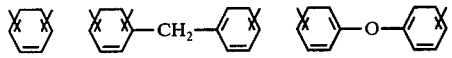

or ethylene, propylene, butylene, or

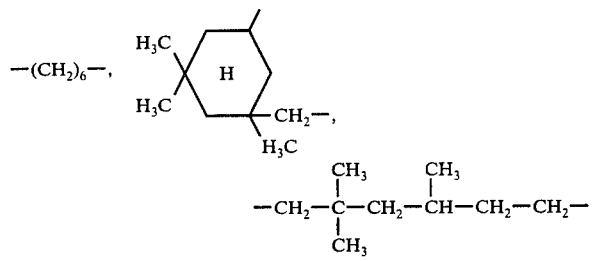

These groups may carry one or more substituents, e.g. at least one selected from alkyl, alkoxy or haloalkyl groups each with up to 5 C - atoms, or nitro groups, halogen, especially F, Cl, Br, e.g. —CH$_3$, —C$_2$H$_5$, —OCH$_3$, —OC$_2$H$_5$ or CF$_3$, and wherein several aromatic rings can be linked by — CH$_2$ —, —O—, —S—, —S—S—, —SO$_2$, —CO— or —N—N—.

If monomeric products are desired, at least one monofunctional reaction component will be used as starting material, e.g. monoisocyanates or monooxamidate esters.

Preferably not more than 5 H-atoms are substituted by such groups in each radical R′′′.

R$^{IV}$ and R$^V$ in the oxamidate esters used are alkyl groups with up to 6 carbon atoms, preferably —CH$_3$, —C$_2$H$_5$, —C$_4$H$_9$, phenyl groups which can be substituted with the aforenamed alkyl groups. Suitable tri- or tetrahydric isocyanates are e.g. 2,4,6-triisocyanatotuene, 4,4′,4′′-triisocyanatotriphenylmethane, 2,4,4′′-triisocyanatodiphenylmathane, 2,2′, 5,5′-tetraisocyanatodiphenyl methane, or trihydric isocyanates of formula

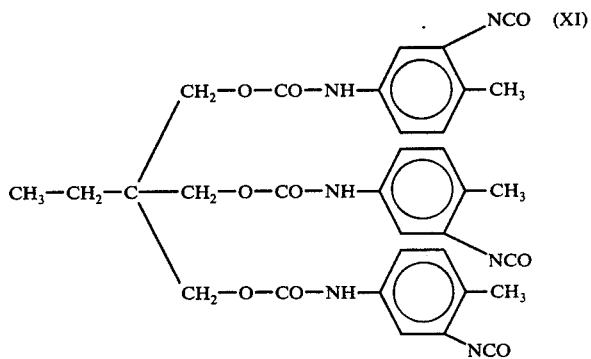

which may be obtained, for example, by addition of trimethylolpropane to tolylene diisocyanate, an isocyanate which may be prepared by reaction of hexamethylenediisocyanate and water, of formula

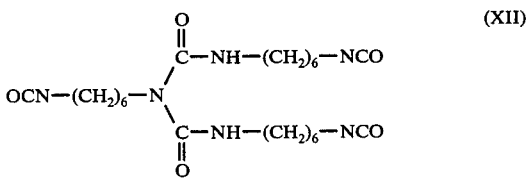

or isocyanates with up to four free isocyanate groups of formula

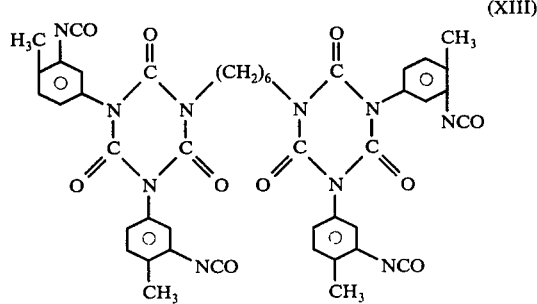

such as may be prepared e.g. by reacting tolylene diisocyanate and hexamethylene diisocyanate.

Also, the tri- and tetraisocyanates can comprise the same above-stated substituents as the diisocyanates.

In place of the free isocyanates, also compounds forming isocyanates can be used, e.g. diphenylmethane-4,4′-bis(carbamino acid phenyl ester), diphenylethane- 4,4'-bis(carbamic acid butyl ester) or diphenyl-4,4'-bis(-carbamino acid diethylamide).

The polyisocyanates are generally reacted with the bis-oxamidates in the mol ratio of 1 : 0.5 to 4, preferably 1 : 0.8 to 2.2, in particular 1 : 0.9 to 1.5. The reaction can take place in the melt, particularly in the presence of solvents, preferably first in the melt and then in phenolic solvents. The reaction can take place e.g. 1) in such solvents in which the reaction products of the invention are insoluble, e.g. in ligroin, benzene, toluene, xylene, chlorobenzene, nitrobenzene, cyclohexane, ethyl acetate, butyl acetate or 2) also in those solvents in which the reaction products are soluble, such as N,N'-dimethylformamide, N,N'-dimethylacetamide, dimethylsulphoxide, N-methylpyrrolidone, N,N',N''-hexamethyl phosphoric acid triamide, phosphoric acid-tris-(dimethylamide), cyclohexanone, isophorone, acetophenone, or in phenols with up to 10 carbon atoms, e.g. phenol, cresol or xylenol.

In addition to the solvents already mentioned, the products are also soluble in ketones, such as acetone, methylethylketone, or dibutylketone.

A further advantage of the present process resides in the possibility of synthesising one and the same asymmetrically substituted 2,4,5-triketoimdazolidine from different starting materials. Thus e.g. the following compound

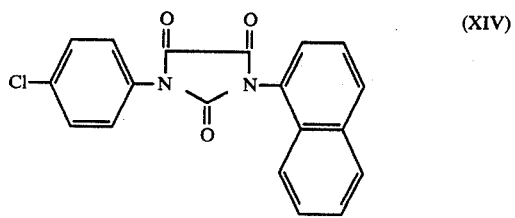

(XIV)

can on the one hand be prepared from p-chlorophenylisocyanate and ethyl N-(1-naphthyl)-oxamidate or on the other hand from 1-naphthylisocyanate and methyl N-(p-chlorophenyl)-oxamidate. It thus becomes possible to select the most favourable reaction components in each case.

The reaction according to the invention can take place in the absence or advantageously in the presence of solvents at temperatures from minus 20° to plus 280° C, preferably at 0° to 180° C. The reaction is exothermic and proceeds in many cases even at room temperature or at a slightly elevated temperature, e.g. even at 40° to 50° C. For completing the reaction and when using less reactive components, e.g. some isocyanates, heating can at times be recommended. It is also possible to react the starting materials in the melt and thereafter, if desired, in phenolic solvents. Products of a particularly high quality are thus obtained.

The reaction according to the invention can take place with or without catalysts. As catalysts basically all those are suitable which catalyse other reactions of isocyanates with compounds having reactive hydrogen atoms. Examples include tertiary bases, such as amines, e.g. triethylamine, tributylamine, N-isobutyl morpholine, pyridine, N-methylpiperidine, N,N-dimethylaniline, triethylenediamine, triphenylphosphine and trimorpholinophosphine or mixtures thereof. Further catalysts are e.g. lithium methoxide, sodium ethoxide, potassium tert.butoxide, as well as organic tin compounds, such as dibutyl tin oxide, dimethyl tin stearate, dibutyl tin glycolate, dibutyl tin dilaurate, diphenyl tin oxide, ferrocene (dicyclopentadienyl-iron (II)), metal chelates, such as iron acetylacetonate or cobalt complexes, or mixtures of any of the aforementioned compounds.

The yields of N,N'-disubstituted 2,4,5-triketoimidazolines in the present process vary generally between 65 and 98% of theory.

The monomeric and polymeric, especially the low-molecular weight compounds prepared according to the invention are valuable intermediates for organic syntheses. They may be used as starting materials for the preparation of pharmaceuticals, pest control agents, such as insecticides, fungicides, mycocides and bactericides, for the synthesis of dyestuffs and synthetic resins and for stabilising high molecular weight substances, particularly polymerisation and condensation resins, e.g. by admixing these resins with a stabilizing amount of a polymer compound as defined herein.

The products and polymers prepared according to the invention are also suitable in particular for the coating of metallic shaped articles, such as wires, metal sheets, plates and pipes, it being immaterial whether the application takes place in the powder form or in solution. They can, however, also be applied in the same way to ceramic shaped articles. After the thermal polycondensation, well-adherent and thermally stable coatings are obtained on these articles. The compounds of the invention are also suitable, however, especially in the powder form, and after mixing them with fillers, e.g. glass flour, glass fibres, asbestos fibres, metal powders or metal chips, for the production of moulded articles according to the hotpress process. Furthermore glass-clear foils and films as well as fibres can be produced therefrom. By suitable means, e.g. the addition of expanding agents, the products can be converted to a foam-like material which is stable at high temperatures. The products obtained according to the invention are also suitable as stabilisers for polymeric products, especially for polymerisation and/or polycondensation resins. They can, however, also be mixed with such polymers including polymerisation and/or polycondensation resins having heterocyclic groups, at temperatures between minus 10 to plus 250° C, preferably at +20° to +190°, in a solution, in the melt or in the solid phase, and worked up further to moulded articles or coatings.

In order that the invention may be better understood, the following examples are given by way of illustration only.

EXAMPLE 1

N-(p-Chlorophenyl)-N'-butyl-2,4,5-triketoimidazolidine:

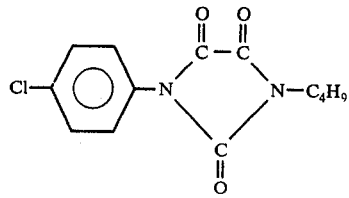

22.8 g (0,1 mol) of ethyl p-chlorophenyl oxamidate are heated for 5 hours on an oil bath at 150° C with 19.8 g (0.2 mol) of butyl isocyanate, 10 ml of xylene and 1 ml of triethylamine. The initially clear solution assumes a yellowish colour after some time and becomes cloudy. After completion of the reaction, the reaction mixture is diluted with 30 ml of ligroin and cooled to 10° C. The precipitated paste of crystals is filtered with suction and washed with cold ligroin/toluene (1:1). After drying in vacuo, the title compound, (16,4 g; 64% of theoretical yield), is obtained in the form of small glossy plates.

EXAMPLE 2

N,N'-Diphenyl-2,4,5-triketoimidazolidine (diphenylparabanic acid):

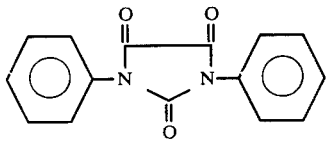

193 g of ethyl N-phenyl oxamidate (1 mol) together with 238 g (2 mol) of phenyl isocyanate are melted with stirring for 7 hours at 150° C. The mixture assumes a greenish-yellow colour and crystals start to separate, 1000 ml of ligroin and 400 ml of toluene are then added. After boiling for a short while, the reaction mixture is cooled to 20° C. The paste of separated crystals is filtered with suction and washed with ligroin/toluene (1:1). After drying at 120° C, 240 g of the title compound are obtained (Yield: 90% of theory). Melting point: 203°-204° (literature: 204° C).

The mixed melting point and the infra red spectrum proved this compound to be identical with diphenylparabanic acid prepared according to conventional processes.

| Analysis: | found | calculated |
|---|---|---|
| C | 67.60 % | 67.65 |
| H | 3.92 | 3.79 |
| N | 10.43 | 10.52 |
| O | 18.05 | 18.04 |
| molecular weight | 259 | 266 (Rast method) |

IR spectroscopy is highly suitable for following the course of the reaction. The triketoimidazolidine ring shows an extremely characteristic band grouping at 1789 cm$^{-1}$
1736 cm$^{-1}$
1493 cm$^{-1}$
1399 cm$^{-1}$
1208 cm$^{-1}$ which remains relatively resistant to displacements, even by substituents. Moreover, the cyclisation is manifested by the disappearance of the —NH—bands at 3300 cm$^{-1}$. When reference is made in the following examples to the IR-spectroscopic identification, this relates in most cases to the above-stated frequencies.

EXAMPLE 3

N,N'-Diphenyl-2,4,5-triketoimidazolidine 193 g of ethyl N-phenyloxamidate and 238 g (2 mol) of phenylisocyanate are stirred with 1000 ml of benzene at 25° C and mixed, accompanied by good cooling, with 3 ml of triethylamine. The temperature rises to 55°-60° C. After a short while, the separation of the imidazoline derivative starts. For completing the reaction, the reaction mixture is boiled under reflux for a further hour and then diluted with 600 ml of ligroin. After cooling to 15° C the crystals formed are filtered off with suction.

Yield of the title compound: 231 g = 87% of theory, m.p. = 203° C. Ethyl phenylcarbamate can be isolated from the mother liquor after concentration and was identified by means of the mixed melting point (m.p. = 52° C, no depression) and the I.R. spectrum.

EXAMPLE 4

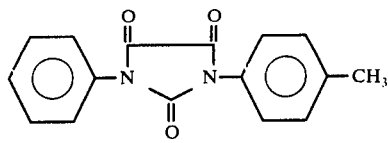

N-(p-Tolyl)-N'-phenyl-2,4,5-triketoimidazolidine 207 g of ethyl N-(p-tolyl)-oxamidate (1 mol) m.p. 86° C, and 238 g of phenylisocyanate (2 mol) are stirred with 700 ml of n-heptane and 300 ml of toluene, 4 ml of tri-n-butylamine being added with cooling. The reaction mixture warms up to about 50° C. After cooling of the reaction mixture, heating at 50° C on a water bath is continued for two further hours. The reaction product crystallises after a short time on standing in a refrigerator. After filtering off the crystals with suction and washing them with a small amount of ligroin, 205 g of the title compound are obtained (Yield: 73% of theory) M.p. = 159° C.

| Analysis | found | calculated |
|---|---|---|
| C | 68.64 % | 68.56 % |
| H | 4.26 % | 4.30 % |
| O | 17.00 % | 17.13 % |
| N | 10.10 % | 10.01 % |
| molecular weight | 273 | 280 |

The I.R. spectrum indicates the triketoimidazolidine structure.

EXAMPLE 5

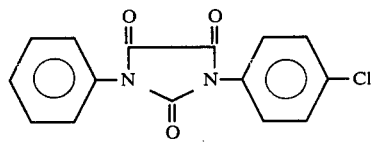

N-(p-Chlorophenyl)-N'-phenyl-2,4,5-triketoimidazolidine 193 g of ethyl N-phenyloxamidate (1 mol) and 307 g of p-chlorophenyl isocyanate (2 mol) are stirred with 2000 ml of toluene at 50° C until the components are dissolved. 3.5 ml of N-methylpiperidine dissolved in 50 ml of toluene are then added dropwise. The vigorous reaction is tempered by cooling. The mixture is then boiled for 15 minutes, mixed with 5 g of activated charcoal and filtered hot. After cooling, the separated crystals are filtered off with suction and dried at 130° C. Yield: 239 g (79.5% of theory), m.p. = 205 − 206° C.

| Analysis: | found | calculated |
|---|---|---|
| N | 9.27 % | 9.32 % |
| Cl | 11.83 % | 11.79 % |
| molecular weight | 293 | 301 |

EXAMPLE 6

N-(p-Chlorophenyl)-N'-phenyl-2,4,5-triketoimidazolidine:

227.5 g of ethyl p-chlorophenyloxamidate (1 mol), m.p. 154° C, and 238 g of phenylisocyanate (2 mol) are heated with 2500 ml of toluene at 70° C and 3 ml of triethylamine are added. The reaction mixture which is homogeneous is then boiled for 1 hour under reflux. 5 g of activated charcoal are added and the mixture is filtered hot. The reaction product crystallises after cooling and is filtered off with suction and dried at 180° C. Yield: 217 g (72% of theory). M.p. = 205° C.

Analysis: the substance is identical with that prepared according to Example 5. The mixed melting point showed no depression. The IR-spectra were identical.

EXAMPLE 7

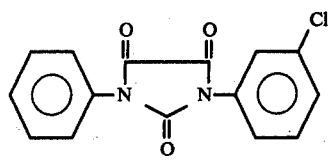

N-(m-Chlorophenyl)-N'-phenyl-2,4,5-triketoimidazolidine 227.5 g of ethyl N-(m-chlorophenyl)-oxamidate (1 mol), m.pt. 168° C, and 238 g of phenylisocyanate (2 mol) are heated with 1000 ml of toluene until dissolved and 5 ml of N-isobutyl morpholine added, with cooling. The reaction mixture is then boiled under reflux for 30 minutes, mixed with 5 g of activated charcoal, filtered hot and cooled in a refrigerator. The crystals formed are filtered off with suction, washed with ligroin/toluene (1:1) and dried at 140° C.

Yield: 214.5 g (71% of theory). M.p. 181°–183° C.

After addition of 250 ml of ligroin, 40 g of impure material (m.P. 174° – 178° C) can be isolated from the mother liquor. Purification can take place by recrystallisation from isopropanol.

| Analysis: | found | calculated |
|---|---|---|
| N | 9.30 % | 9.32 % |
| Cl | 11.83 % | 11.79 % |
| molecular weight | 289 | 301 |

The IR-spectrum shows the band groupings stated in Example 2. If the mentioned oxamidate is substituted by 1 mol of N-(m-cyanophenyl)-oxamidate or of N-(m-cyclohexylphenyl)-oxamidate the corresponding cyano- or cyclohexyl-substituted products are obtained.

EXAMPLE 8

236 g (78.5% of theory) of N-(m-chlorophenyl)-N'-phenyl-2,4,5-triketoimidazolidine are obtained from 193 g of ethyl N-phenyl-oxamidate (1 mol) and 307 g of m-chlorophenylisocyanate (2 mol) according to the method described in Example 7. The identity was confirmed by the mixed melting point and the IR-spectrum.

EXAMPLE 9

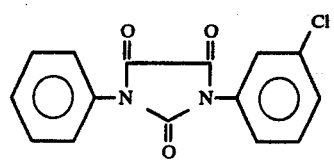

N-(p-Chlorophenyl)-N'-(m-chlorophenyl)-2,4,5-triketoimidazolidine

Analysis:
227.5 g of ethyl N-(p-chlorophenyl)-oxamidate (1 mol)
307.0 g of m-chlorophenyl isocyanate (2 mol)
1200 ml toluene
2 ml of triethylamine
2 ml of pyridine
Reaction conditions were as in Example 2.

Yield: 300 g (89% of theory). M.p. = 222°–224° C after a single recrystallisation from toluene/ligroin (8:2).

| Analysis: | found | calculated |
|---|---|---|
| N | 8.30 % | 8.36 % |
| Cl | 21.05 % | 21.15 % |

EXAMPLE 10

N-(m-trifluoromethylphenyl)-N'-phenyl-2,4,5-triketoimidazolidine:

261 g of ethyl N-(m-trifluoromethylphenyl)-oxamidate (1 mol), m.p. = 116° C, and 238 g of phenylisocyanate (2 mol) are boiled under reflux for 2 hours with 750 ml of toluene, 2 ml of triethylamine and 2 ml of N,N-dimethylaniline. 500 ml of toluene and 500 ml of ligroin are then added, boiled with 5 g of activated charcoal, filtered hot and cooled to 10° C.

The paste of crystals is filtered with suction.

Yield: 229 g = 68.5% of theory. M.p. = 189°–191° C. After a single recrystallisation the melting point rises to 193° C.

| Analysis: | found | calculated |
|---|---|---|
| N | 8.38 % | 8.38 % |
| F | 16.92 % | 17.05 % |
| molecular weight | 327 | 334 |

EXAMPLE 11

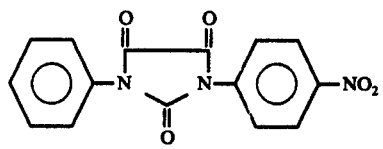

N-(p-Nitrophenyl)-N'-phenyl-2,4,5-triketoimidazolidine 238 g of ethyl N-(p-nitrophenyl)-oxamidate (1 mol; m.p. = 165° C),
238 g of phenylisocyanate (2 mol), 5 ml of triethylamine, 500 ml of chloroform and 1000 ml of toluene are boiled under reflux for 6 hours. After cooling, the yellowish, crystalline material is filtered off with suction and washed with toluene/ligroin (1:2).

Yield 221 g. (71.5% of theory). M.p. = 198°-201° C. Light-yellow crystals m.pt. = 208°-209° C are obtained after recrystallisation from xylene;

| Analysis: | found | calculated |
|---|---|---|
| N | 13.47 % | 13.50 % |
| molecular weight | 307 | 311 |

EXAMPLE 12

19.6 g of N-(p-nitrophenyl)-N'-phenyl-2,4,5-triketoimidazolidine are obtained from 19.3 g of ethyl N-phenyloxamidate (0.1 mol), 32.8 g of p-nitrophenylisocyanate (0.2 mol), 150 ml of toluene, 30 ml of chloroform and 0.3 ml of pyridine according to the method described in Example 11. Yield: 63% of theory. M.p. = 208° C. Identification is by mixed melting point and IR-spectrum, in comparison with the product of Example 11.

EXAMPLE 13

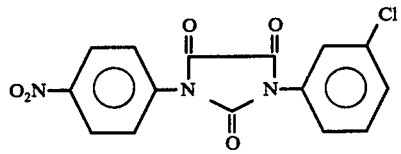

N-(p-Nitrophenyl)-N'-(m-chlorophenyl)-2,4,5-triketoimidazolidine:

4.76 g of ethyl N-(p-nitrophenyl)-oxamidate (0.020 mol) are boiled under reflux for 2 hours with 6.14 g of m-chlorophenylisocyanate (0.040 mol), 40 ml of toluene and 5 drops of triisopropylamine. After cooling, the paste of separated crystals is filtered with suction. The precipitate is recrystallised from 210 ml xylene.

Yield: 5.9 g. = 85% of theory m.p. = 220° to 222° C.

| Analysis: | found | calculated |
|---|---|---|
| C | 52.10 % | 52.11 % |
| H | 2.41 % | 2.34 % |
| O | 23.02 % | 23.14 % |
| N | 12.12 % | 12.16 % |
| Molecular weight | 352 | 345.7 |

EXAMPLE 14

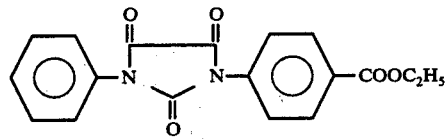

N-(p-Carboxyethyl)-N'-phenyl-2,4,5-triketoimidazolidine 26.5 g. of ethyl N-(p carboxyethylphenyl)-oxamidate (0.1 mol), m.p. = 125.5° C, 23.8 g. of phenyl isocyanate (0.2 mol), 130 ml. of toluene, 5 ml of chlorobenzene and 0.2 g. of triphenylphosphine are boiled under reflux for 2 hours. After addition of 100 ml. of ligroin, the imidazolidine derivative crystallises out on cooling.

Yield: 32.5 g. (96% of theory). M.p. = 182°-194° C.

After recrystallisation from ligroin/toluene (1:1), 23.6 g. of product of m.p. 188.5° C are obtained.

| Analysis: | found | calculated |
|---|---|---|
| N | 8.29 % | 8.27 % |
| molecular weight | 329 | 338.3 |

EXAMPLE 15

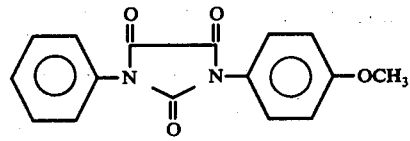

N-(p-Methoxyphenyl)-N'-phenyl-2,4,5-triketoimidazolidine 22.3 g. ethyl N-(p-methoxyphenyl)-oxamidate (0.1 mol) and 23.8 g. of phenylisocynate (1.2 mol) are boiled under reflux for 1 hour with 100 ml. of toluene and 50 ml. of ligroin with addition of 0.4 g. of trimorpholinophosphine. 2 g. of activated charcoal are added to the hot reaction mixture which is boiled for a short while and then filtered. After cooling to 10° C, colourless needles crystallise out. They are filtered off with suction and washed with a small amount of ligroin. Yield: 23.0 g (78% of theory). M.p. = 129° - 131° C.

| Analysis | found | calculated |
|---|---|---|
| C | 64.78 % | 64.85 % |
| H | 4.18 % | 4.09 % |
| N | 9.59 % | 9.45 % |
| molecular weight | 314 | 296.3 |

EXAMPLE 16

19.7 g of N-(p-methoxyphenyl)-N'-phenyl-2,4,5-triketoimidazolidine are obtained from 19.3 g of ethyl N-phenyloxamidate (0.1 mol) 29.8 g of p-methoxyphenylisocyanate (0.2 mol), 150 ml of toluene, 50 ml of ligroin and 0.5 ml of triethylamine under the conditions of Example 15.

Yield: 66.5% of theory. M.p. 135° - 136° C.

On melting, a sample showed no depression with respect to a sample of the product of Example 15. The IR-spectra were identical.

EXAMPLE 17

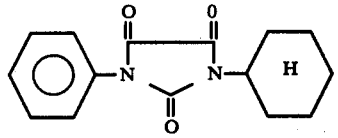

N-Phenyl-N'-cyclohexyl-2,4,5-triketoimidazolidine 19.3 g of ethyl N-phenyloxamidate (0.1 mol), 24.8 g of cyclohexylisocyanate (0.2 mol) and 1 ml of triethylamine are heated for one hour on a glycerol bath. The mixture assumes a darkbrown colour. After addition of 50 ml of toluene and 50 ml of ligroin, the mixture solidifies to a crystalline mass at 10° C. After filtration under suction 18 g (66.5% of theory) of crystals are obtained. M.p. = 133° - 140° C.

After recrystallisation from isopropanol, the melting point rises to 148° - 149° C.

| Analysis: | found | calculated |
|---|---|---|
| C | 66.50 % | 66.40 % |
| H | 5.25 % | 5.58 % |
| O | 17.71 % | 17.69 % |
| N | 10.54 % | 10.33 % |
| molecular weight | 280 | 271.3 |

In using 0.2 mol of methyl-cyclohexylisocyanate as a starting material the corresponding N-phenyl-N'-methylcyclohexyl compound is obtained.

EXAMPLE 18

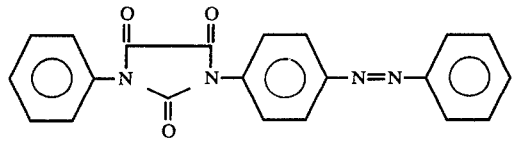

N-(p-Benzene-azo-phenyl)-N'-phenyl-2,4,5-triketoimidazolidine 29.7 g. of ethyl N-(benzene-azo-phenyl)-oxamidate (0.1 mol), m.p. = 154° C and 23.8 g. of phenylisocyanate (0.2 mol) are heated under reflux for 4 hours with 100 ml toluene and 0.3 ml triethylamine. 100 ml. of ligroin are then added. The separated, orange-red crystals are filtered off with suction, washed with ligroin/toluene (2:1) and dried at 120° C. Yield: 36.5 g. (98.5% of theory) m.p. 200° C.

Even after recrystallisation, the melting point remained unchanged.

| Analysis: | found | calculated |
|---|---|---|
| C | 68.09 % | 68.10 % |
| H | 4.04 % | 3.81 % |
| O | 12.96 % | 12.96 % |
| N | 15.25 % | 15.13 % |
| molecular weight | 355 | 370.4 |

EXAMPLE 19

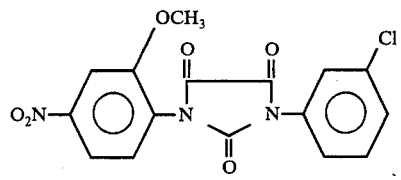

N-(4-Nitro-2-methoxyphenyl)-N'-(m-chlorophenyl)-2,4,5-triketoimidazolidine 26.8 g. of ethyl N-(4-nitro-2-methoxyphenyl)-oxamidate (0.1 mol), m.p. = 145° C, and 30.7 g. of m-chlorophenylisocyanate (0.2 mol) are boiled under reflux for 20 minutes with 2 ml. of tri-n-butylamine, 150 ml. toluene and 100 ml. of ligroin. After cooling to 20° C, the reaction mixture solidifies, 28.5 g. (76% of theory) of product are obtained by filtering off the crystals with suction. M.p. = 176°-178° C; pale yellowish needles (m.p. = 181° C) are obtained after recrystallisation from toluene/ligroin (1.5:1)

| Analysis: | found | calculated |
|---|---|---|
| N | 11.24 % | 11.19 % |
| Cl | 9.36 % | 9.42 % |
| molecular weight | 369 | 375.7 |

EXAMPLE 20

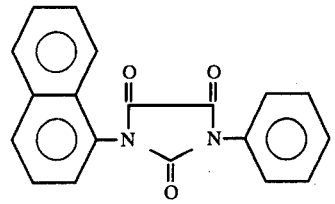

N-(1-Naphthyl)-N'-phenyl-2,4,5-triketoimidazolidine 24.3 g of ethyl N-(1-naphthyl)-oxamidate (0.1 mol), m.p. = 105°-108° C, are boiled for 45 minutes with 23.8 g of phenylisocyanate (0.2 mol) 150 ml of toluene, 5 ml of N,N-dimethylformamide and 0.2 g of lithium methylate. The separation of crystals starts even in the hot. After cooling, the precipitate is filtered off with suction and washed with ligroin/toluene (1:1). After drying at 150° C, 26.0 g (82.5% of theory) of crystals are obtained, m.p. = 203°-206° C. After recrystallisation from n-butanol, small white needles with a melting point of 207° C are obtained.

| Analysis: | found | calculated |
|---|---|---|
| C | 72.21 % | 72.14 % |
| H | 3.94 % | 3.83 % |
| N | 8.79 % | 8.86 % |

EXAMPLE 21

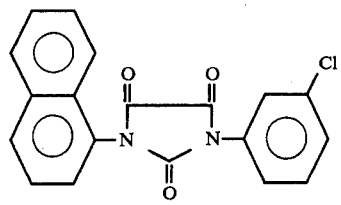

N-(1-Naphthyl)-N'-(m-chlorophenyl)-2,4,5-triketoimidazolidine 24.3 g of ethyl N-(1-naphthyl)-oxamidate (0.1 mol) m.p. = 106° C, and 30.7 g of m-chlorophenylisocyanate (0.2 mol) are mixed at room temperature. A solution of 2 ml of triethylamine in 30 ml of toluene is then quickly stirred in. The mixture heats up considerably. After the exothermic reaction has subsided, the mixture is diluted with 100 ml of toluene and 100 ml of ligroin and the paste of crystals filtered with suction.

Yield: 29.0 g — (82.5% of theory).

M.p. = 163° - 165° C.

White crystals of m.p. = 169°-170° C are obtained after recrystallisation from ethyl alcohol.

| Analysis: | found | calculated |
|---|---|---|
| N | 7.86 % | 7.98 % |
| Cl | 10.20 % | 10.11 % |
| molecular weight | 342 | 350.8 |

EXAMPLE 22

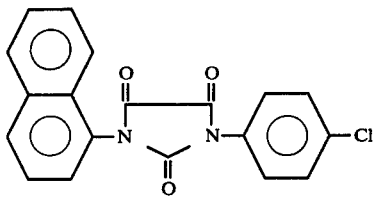

N-(1-Naphthyl)-N'-(p-chlorophenyl)-2,4,5-triketoimidazolidine 21.4 g. of methyl N-(p-chlorophenyl)-oxamidate (0.1 mol), m.p. 158° C, and 33.8 g. of 1-naphthylisocyanate (0.2 mol) are boiled under reflux for 20 minutes with 120 ml. of xylene and 1 ml. of N,N-dimethylaniline. The crystals separated after cooling are filtered off with suction.

Yield: 28.5 g (81% of theory).
M.p. = 240°-244° C.
After recrystallisation from xylene: m.p. 247°-248° C.

| Analysis | found | calculated |
|---|---|---|
| C | 65.12 % | 65.06 % |
| H | 3.04 % | 3.16 % |
| N | 7.91 % | 7.98 % |
| Cl | 10.26 % | 10.11 % |
| molecular weight | 366 | 350.8 |

EXAMPLE 23

N-(4-Nitro-2-methoxyphenyl)-N'-(m-chlorophenyl)-2,4,5-triketoimidazolidine 29.6 g. of butyl N-(4-nitro-2-methoxyphenyl)-oxamidate (0.1 mol) m.p. 122° C, 30.7 g. of m-chlorophenylisocyanate (0.2 mol) and 200 ml. of toluene are heated for 2 hours at 110° C with 0.5 ml. of triisopropylamine, 0.5 g. of activated charcoal are added to the clear, hot solution which is then filtered. After addition of 150 ml. of ligroin, the product crystallises out in yellowish husks. Yield: 26.5 g. (70.5% of theory) m.p. = 176°-178° C.

After recrystallisation from ligroin/toluene (1:2), the melting point rises to 181°-182° C. No depression of the melting point is observed on mixing with the compound of Example 19. The IR-spectra are likewise identical.

EXAMPLE 24

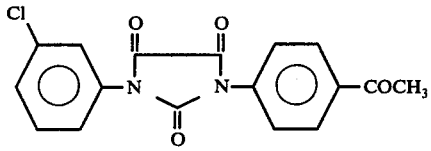

N-(4-Acetylphenyl)-N'-(m-chlorophenyl)-2,4,5-triketoimidazolidine 23.5 g of ethyl N-(4-acetylphenyl)-oxamidate (0.1 mol), m.p. = 148° C, and 30.7 g of m-chlorophenylisocyanate (0.2 mol) are stirred at room temperature with 300 ml of toluene and 0.5 ml of triethylamine. After a few minutes, the temperature of the mixture rises to about 40° C. The reaction mixture is stirred for one hour and the crystals, precipitated on cooling, are filtered off with suction.

Yield: 30 g — (67% of theory).
M.p. = 207°-208° C.

After recrystallisation from xylene, the melting point rises to 211°-212° C. The IR-spectrum shows the characteristic absorption maxima (see example 2).

| Analysis: | found | calculated |
|---|---|---|
| N | 8.15 % | 8.17 % |

EXAMPLE 25

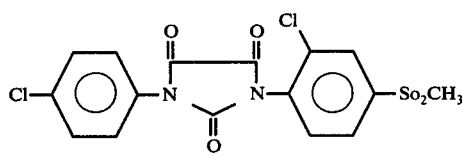

N-(4-Methylsulphonyl-2-chlorophenyl)-N'-(p-chlorophenyl)-2,4,5-triketoimidazolidine 30.6 g of ethyl N-(4-methylsulphonyl-2-chlorophenyl)-oxamidate (0.1 mol) m.p. = 160° C, are boiled under reflux for 2 hours with 30.7 g of p-chlorophenylisocyanate (0.2 mol) and 200 ml of toluene with addition of 0.5 g of tris(carboxyethyl)-phosphine. The separated solid product is filtered off after cooling, washed with toluene/alcohol and dried at 150° C.

Yield: 36.0 g (95.5% of theory).

Small fine white needles, m.p. = 249°-251° C, are obtained after recrystallising from a xylene/cyclohexanone mixture.

| Analysis: | found | calculated |
|---|---|---|
| N | 7.36 % | 7.41 % |
|  | 8.31 % | 8.49 % |
|  | 9.43 % | 9.39 % |

EXAMPLE 26

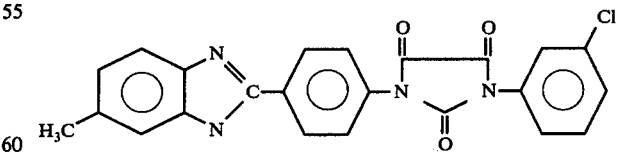

N-[4-(6-Methyl-benzothiazolyl)-phenyl]-N'(m-chlorophenyl)-2,4,5-triketoimidazolidine 34.0 g of ethyl N-[4-(6-methyl-benzothiazolyl)-phenyl] oxamidate (0.1 mol), m.p. = 194° C, 30.7 g of m-chlorophenylisocyanate (0.2 mol) 500 ml of toluene and 1 ml of triethylamine are boiled under reflux for 25 minutes. The paste of crystals formed ist filtered with suction, after cooling, and washed with cold toluene.

Yield: 44.0 g — (95% of theory).

M.p. = 268°–271° C.

After recrystallisation the m.p. rises to 279°–280° C.

| Analysis: | found | calculated |
|---|---|---|
| N | 9.33 % | 9.38% |

EXAMPLE 27

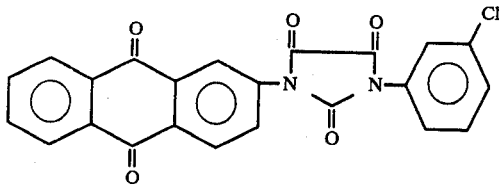

N-(2-Anthraquinonyl)-N'-(m-chlorophenyl)-2,4,5-triketoimidazolidine 32.3 g of ethyl N-(2-anthraquinonyl)-oxamidate (0.1 mol. m.p. = 211° C) and 30.7 g of m-chlorophenylisocyanate (0.2 mol) are boiled under reflux for 5 hours with 300 ml of xylene, 5 ml of N-methylpyrrolidone and 0.5 ml of tri-n-butylamine. After cooling, the product crystallises out in yellow crystals. These are filtered with suction and washed with warm toluene. Yield: 42.0 g = (96% of theory). After recrystallising from xylene/chlorobenzene the product melts at 268°–269° C.

The IR-spectrum shows no ester bands and no -HN- bands.

EXAMPLE 28

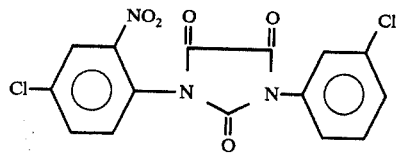

N-(2-Nitro-4-chlorophenyl)-N'-(m-chlorophenyl)-2,4,5-triketoimidazolidine 25.9 g of methyl N-(2-nitro-4-chlorophenyl)-oxamidate (0.1 mol), m.p. = 133° C, and 30.7 g of m-chlorophenylisocyanate (0.2 mol) are dissolved in 150 ml of toluene and, after addition of 1 ml of triethylamine, allowed to stand for 2 hours. The product crystallises out after a short standing in a refrigerator at 5° C. It is filtered off with suction, washed with a small amount of ligroin and dried at 100° C.

Yield: 31.0 g = (82% of theory).

M.p. = 178°–180° C.

M.p. after recrystallisation from toluene/ligroin (1:1) 183°–184° C.

| | Analysis: | |
|---|---|---|
| | found | calculated |
| C | 47.34% | 47.39% |
| H | 1.92% | 1.86% |
| O | 21.11% | 21.04% |
| N | 11.07% | 11.05% |

| | Analysis: | |
|---|---|---|
| | found | calculated |
| molecular weight | 369 | 380.1 |

EXAMPLE 29

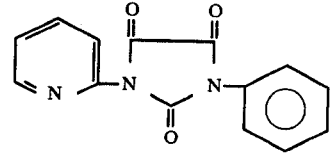

N-(2-Pyridyl)-N'-phenyl-2,4,5-triketoimidazolidine 19.4 g of ethyl N-(2-pyridyl)-oxamidate (0.1 mol) (crude product) are dissolved with 23.8 g of phenylisocyanate (0.2 mol) in 80 ml of toluene at 30° C. After addition of 0.3 ml of triethylamine a vigorous reaction accompanied by a rise of temperature to 70° C takes place. The mixture becomes viscous. After diluting with 40 ml of ligroin and 20 ml of toluene, crystallisation starts. After standing for 6 hours in a refrigerator at 5° C, the paste of crystals is filtered with suction and washed with a small amount of ligroin.

Yield: 24.4 g. (91% of theory), m.p. = 154°–155° C after recrystallisation from toluene m.p. = 163° C.

| | Analysis: | |
|---|---|---|
| | found | calculated |
| C | 62.80 % | 62.88 % |
| H | 3.54 % | 3.40 % |
| O | 18.03 % | 17.98 % |
| N | 15.79 % | 15.74 % |
| molecular weight | 269 | 267 |

EXAMPLE 30

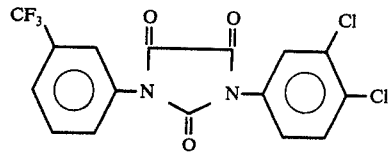

N-(3-Trifluoromethylphenyl)-N'-(3,4-dichlorophenyl)-2,4,5-triketoimidazolidine 26.1 g. of ethyl-N-(3-trifluoromethylphenyl)-oxamidate (0,1 mol), m.p. 116° C, and 37.6 g. of 3,4-dichlorophenylisocyanate (0.2 mol) are boiled under reflux for 80 minutes with 200 ml. of toluene, 1 ml. of tri-morpholino-phosphine and 0.5 ml. of tri-n-butylamine. After cooling, the product crystallises out. The thin and small, white needles are filtered off with suction and wasched with ligroin/toluene (1:1) and, after drying at 120° C, recrystallised from toluene.

Yield: 36.0 g. (89% of theory) m.p. = 230°–231° C.

| | Analysis: | |
|---|---|---|
| | found | calculated |
| C | 47.62 % | 47.66 % |
| H | 1.80 % | 1.74 % |

| Analysis: | |
|---|---|
| found | calculated |
| N 6.83 % | 6.95 % |

EXAMPLE 31

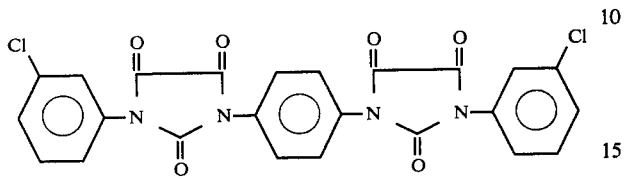

1,4-Bis-[N-(N'-(3-chlorophenyl)-2,4,5-triketoimidazolidyl)]-benzene 30.8 g of N,N'-bis-ethoxalyl-p-phenylenediamine (0.1 mol), m.p. = 212° C, and 61.4 g of m-chlorophenylisocyanate (0.4 mol) are heated at 80° C with 350 ml of xylene and 60 ml of N,N-dimethylacetamide. A solution of 1 g of tri-n-butylamine in 20 ml of alcohol is then queckly stirred in. The temperature then rises by a few degrees. The reaction mixture is then boiled under reflux for 5 hours. The separation of a heavy, light-yellow powder starts after a few minutes. The product is filtered off after cooling, washed with hot xylene and hot n-butanol and dried at 150° C.

Yield: 51.5 g (98% of theory). No melting under 360° C. The substance can be recrystallised from cyclohexanone/N-methylpyrrolidone to form colourless microscopically small needles.

| Analysis: | |
|---|---|
| found | calculated |
| Cl 13.62% | 13.56% |

The IR - spectrum clearly shows the band grouping described in Example 2.

Ester bands and —NH-bands are completely absent.

EXAMPLE 32

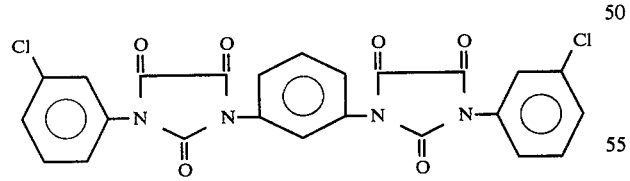

1,3-Bis-[N-(N'-(3-chlorophenyl)-2,4,5-triketoimidazolidyl)]-benzene

The compound is prepared from N,N'-bis-ethoxalyl-m-phenylenediamine and m-chlorophenylisocyanate by the method described in Example 31. In place of N,N-dimethylacetamide, however, 30 ml of N-methyl pyrrolidone are used.

Yield: 94% of theory.

M.p. 304°–306° C (darkening).

EXAMPLE 33

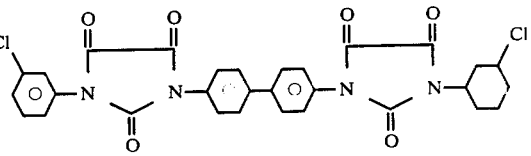

4,4'-Bis-[N-(N'-(3-chlorophenyl)-2,4,5-triketoimidazolidyl)]-diphenyl 38.4 g of N,N'-bis-ethoxalyl-benzidine (0.1 mol), m.p. 218° C, are refluxed for 3 hours with 61.4 g of m-chlorophenylisocyanate (0.4 mol), 600 ml of xylene, 60 ml of N,N',N''-hexamethylphosphoric acid triamide and 2 ml of triethylamine. After cooling, the sandy, yellowish powder is filtered with suction.

Yield: 54.6 g (90% of theory).

No melting below 360° C. The comparison of the IR-spectra of this hexacyclic compound with the pentacyclic compound prepared according to Example 31 shows identity in the bands mentioned in Example 2.

EXAMPLE 34

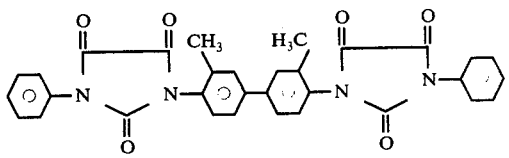

4,4'-Bis-[N-(N'-phenyl)-2,4,5-triketoimidazolidyl]-3,3'-dimethyldiphenyl 41.2 g of N,N'-ethoxalyl-3,3'-dimethyl-benzidine (0.1 mol; m.p. = 179° C), and 47.6 g of phenylisocyanate (0.4 mol) are boiled under reflux for 3 hours with 250 ml of xylene, 50 ml of chlorobenzene and 2.5 ml of tri-n-butylamine. The precipitated product is filtered off with suction, washed with xylene and dried at 180° C.

Yield: 50.0 g (90% of theory).

M.p. 300° C.

M.P. after recrystallisation from cyclohexanone/-dimethylformamide = 304° C.

| Analysis: | |
|---|---|
| found | calculated |
| N 10.47% | 10.56% |

EXAMPLE 35

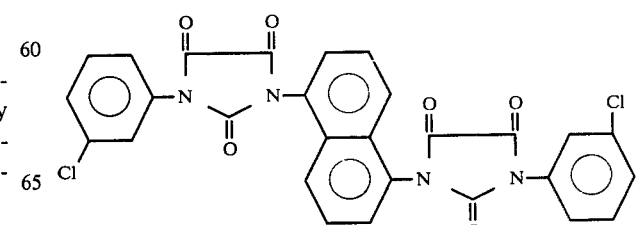

1,5-Bis-[N-(N'-(3-chlorophenyl)-2,4,5-triketoimidazolidyl)]-naphthalene 35.8 g of N,N'-bis-ethoxalyl-naphthylene-1,5-diamine (0.1 mol, m.p. = 213° C) are boiled under reflux for 6 hours with 61.4 g of m-chlorophenylisocyanate (0.4 mol), 500 ml of benzene, 60 ml of dimethyl formamide and 3 ml of triethylamine. The heavy grey powder which separates is filtered off with suction, washed with toluene and isopropanol and dried at 150° C.

Yield: 39.9 g (68% of theory).

No melting below 360° C.

EXAMPLE 36

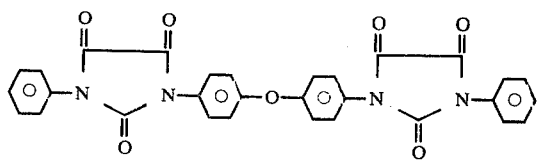

4,4'-Bis-[N-(N'-phenyl)-2,4,5-triketoimidazolidyl]-diphenyl ether 20.0 g of N,N'-bis-ethoxalyl-4,4-diaminodiphenylether (0.05 mol; m.p. 154° C), 100 ml of toluene, 3 ml of N,N'-dimethylacetamide 23.8 g of phenylisocyanate (0.2 mol) and 1 ml of triisopropylamine are heated under reflux for 4 hours. 200 ml of ligroin and 100 ml of toluene are then added and the reaction mixture is filtered hot after addition of 3 g of activated charcoal. The product crystallises out after cooling to about 5° C.

Yield: 25.0 g (91% of theory).

M.p. 267°–272° C.

M.p. after recrystallisation from xylene/ligroin (2:1), m.p. = 278° C.

The IR-spectrum shows band groupings in very good conformity with those described in Example 2. The —NH—bands are absent.

EXAMPLE 37

398 g (1 mol) of bis-N,N'-ethoxalyl-4,4'-diaminodiphenylmethane are first stirred for one hour at room temperature under a protective gas ($N_2$ or $CO_2$) with 252 g (1 mol) of 4,4'-di-isocyanato-diphenyl ether in 250 g of N,N'-dimethylformamide and 400 g of N-methylpyrrolidone. A solution of 10 ml of triethylamine and 0.3 g of cobalt naphthenate in 50 ml of N,N'-dimethylformamide is then added dropwise so that the temperature does not exceed 50° C. After the exothermal reaction has subsided stirring is continued for three further hours. A pale yellow solution is obtained which has a viscosity of 1200–1300 cP (20° C).

If metal sheets are coated in known manner with this solution, and the layer is stoved for 5 minutes at 375° C, clear, elastic, and well adherent coatings having an outstanding resistance to solvents and chemical attack are obtained.

EXAMPLE 38

308 g (1 mol) of 1,4-di-ethoxalylamino-benzene are dissolved at room temperature, with 250 g (1 mol) of 4,4'-diisocyanato-diphenylmethane in 400 g of N,N'-dimethylacetamide, and 158 g of N,N',N''-hexamethylphosphoric acid triamide and 5 ml of triethylamine are added. The temperature then rises to about 70° C. The initially mobile liquid turns gradually more viscous. After the exothermal reaction has subsided, stirring is continued for 2 further hours at 80° C. The terminal viscosity of the solution is 2000 to 2500 cP (20° C).

Copper wires coated with this solution yield, after a thermal treatment for 160 seconds at 430° C, clear, well-adherent coatings with a high chemical thermal stability.

EXAMPLE 39

384 g (1 mol) of 4,4'-di-ethoxalylamino-diphenyl and 202 g (1.2 mol) of 1,6-di-isocyanatohexane are kept for 1 hour at 150° C with 5 g of N-methylmorpholine and 0.5 g of iron acetylacetonate. 293 g of dimethylsulphoxide are then stirred in and stirring is continued for 4 further hours at 100° C.

The pale brown solution obtained yields, on application to metal surfaces and thermal treatment at 240° C, clear, pale brown and elastic coatings.

EXAMPLE 40

400 g (1 mol) of 4,4'-di-ethoxalylamino-diphenyl ether and 174 g (1 mol) of tolylene 2,4-diisocyanate are stirred together at 50° C. 3 ml of tri-n-butylamine are then added. By cooling, the temperature is kept below 80° C. 574 g of N-methylpyrrolidone are then added quickly. After stirring for 5 hours at 70°–80° C, a clear, pale yellow solution of medium viscosity is obtained (1500–1800 cP, 20° C). Upon stoving a coating of this solution on unglazed hard white ware at 420° C, clear, orange-brown, well-adherent coatings of a high thermal stability are obtained.

EXAMPLE 41

412 g (1 mol) of 4,4'-di-ethoxalylamino-3,3-dimethyldiphenyl and 252 g (1.2 mol) of naphthylene-1,5-diisocyanate are stirred homogeneously at 50° C with 150 g of cyclohexanone and 650 g of N-methylpyrrolidone. After addition of 0.5 g of dibutyl tin glycolate and 2 g of triphenylphosphine, the temperature is raised to 180° C. The initially cloudy reaction mixture becomes almost clear in the course of 4 hours. It is filtered through a pressure filter, whereupon a clear, orange-yellow solution is obtained. Clear, hard films are obtained upon stoving this solution on glass plates at 375° C.

EXAMPLE 42

444 g (1 mol) of 4,4-di-ethoxalylamino-3,3-dimethoxydiphenyl are dissolved with stirring in 100 g of N,N'-dimethylaniline and 700 g of N,N.dimethylformamide. A solution of 252 g (1 mol) of 4,4-diisocyanatodiphenyl ether in 1500 ml of xylene is then added at 50° C and the temperature raised to 140° C. The initially clear solution turns more cloudy and the separation of a light-yellow substance starts. After several hours the mixture is cooled to room temperature, and the solid product is filtered off, washed with toluene and dried in vacuo at 70° C.

Yield: 622 g (89% of theory). The pale yellow powder obtained is readily soluble in N,N-dimethylacetamide, dimethylsulphoxide and N-methylpyrrolidone. Upon stoving at 320°–350° C, the solutions yield clear, elastic coatings on metallic surfaces which can only be dissolved in warm, concentrated sulphuric acid.

EXAMPLE 43

308 g (1 mol) of 1,3-di-ethoxalylamino-benzene are dissolved at 35° C under nitrogen as protective gas in 560 g of N-methylpyrrolidone. 250 g (1 mol) of 4,4'-diisocyanato-diphenylmethane are then stirred in. After homogenising well, 5 ml of triisopropylamine and 0.2 g of tris(carboxyethyl)phosphine are added. The temperature rises to about 70° C. The reaction mixture is then stirred until the exothermal reaction subsides and the temperature drops to 50° C. Stirring is continued at this temperature for 3 further hours. The pale yellow viscous solution is suitable in this form for the coating of metallic surfaces. Stoving can take place at 325°–430° C. The clear, brownish-yellow coats are very stable even at high temperatures. The loss of weight amounts to less than 3% at 400° C after 5 minutes in the atmosphere. The thermal continuous load at 325° C in the atmosphere exceeds 15 hours.

EXAMPLE 44

322 g (1 mol) of 1,3-di-ethoxalylamino-2-methylbenzene and 279 g (1.6 mol) of tolylene-2,4-diisocyanate are stirred at room temperature with 400 g of N-methylpyrrolidone, and 50 g of isophorone and 10 g of triethylamine are added. After adding the catalyst, the temperature rises to 50°–60° C. The initially cloudy reaction mixture turns clear. If no heat is supplied, the reaction is completed after stirring for 4–6 hours. The solution obtained may be used for the manufacture of coatings which are highly resistant to changes of temperature.

EXAMPLE 45

400 g (1 mol) of 4,4'-di-ethoxalylamino-diphenyl-ether are stirred at room temperature with 252 g (1 mol) of 4,4'-di-isocyanato-diphenyl ether and 650 g of N-methylpyrrolidone. 7 ml of tri-n-butylamine are added to the pasty mixture. The temperature rises to about 60° C. The mixture is then stirred for 6 hours without any supply of heat. The clear, brownish-yellow solution thus obtained has a viscosity of about 1400 cP (20° C). Clear, pale brown films are obtained by stoving this solution on glass plates for 30 minutes at 360° C. The analysis of the elastic film showed the following values.

|   | found | calculated |
|---|---|---|
| C | 64.67% | 64.28% |
| H | 3.38% | 2.88% |
| O | 22.10% | 22.84% |
| N | 10.00% | 10.00% |
|   | 100.15% | 100.00% | which are consistent with the structure:

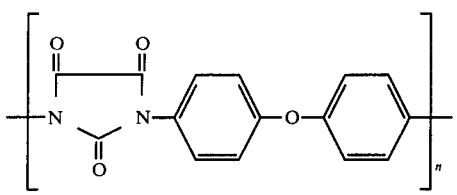

Neither urethane nor ester nor —NH— groups could be traced in the IR-spectrum.

EXAMPLE 46

398 g (1 mol) of 4,4'-di-ethoxalylamino-diphenylmethane are dissolved at 70° C in 800 g of N-methylpyrrolidone and 10 ml of triethylamine are added; 500 g (2 mol) of 4,4'-di-isocyano-diphenylmethane are then added portion-wise. The temperature should not exceed 80°–85° C. After the addition has been completed, stirring is continued for 6 hours at room temperature and the reaction mixture then diluted with 100 g of a mixture of phenol and cresol (ratio 1:1). A clear, yellow solution is obtained which, upon stoving on metallic surfaces at 350°–410° C, yields well-adherent coatings.

EXAMPLE 47

448 g (1 mol) of 4,4'-di-ethoxalylamino-diphenylsulphone are stirred with 250 g of N,N',N''-hexamethylphosphoric acid triamide and 450 g of N-methylpyrrolidone with addition of 10 g of triethylenediamine, whereby a paste is formed. 252 g (1 mol) of 4,4'-diisocyanodiphenyl ether are then so added that the temperature does not exceed 60° C. The initially thin paste thus turns into a clear solution with a moderate viscosity. The reaction is completed by stirring for 8 hours more. Upon heating on metallic surfaces (10 mins., 325° C), the solution yields clear films which are extremely stable to organic solvents.

EXAMPLE 48

796 g (2 mol) of the bis-oxamidate ester of 4,4'-diaminodiphenylmethane are melted with stirring for 6 hours at 140° C with 500 g (2 mol) of 4,4'-diisocyanodiphenylmethane. 1296 g of a cresol mixture and 2 ml of dibutyl tin laurate are then added and the reaction mixture is then heated for a further 3 hours at 200°–210° C. After cooling, a clear, red-brown, highly viscous solution of the polymer is obtained.

Yield: 2500 g.

EXAMPLE 49

800 g (2 mol) of bis-oxamidate of 4,4'-diaminodiphenyl ether are heated for 6 hours at 200°–220° C with a mixture of 375 g of 4,4'-diisocyanato-diphenylmethane, 126 g of 4,4'-diisocyanato-diphenyl ether and 0.3 g. of diazabicyclooctane. The melt is then poured at 160° C on to metal sheets. The material obtained after cooling is pulverised.

Yield: 1280 g. (softening range 120°–135° C).

The yellow powder is readily soluble in aprotnoic solvents, cyclohexanone and phenolic mixtures.

EXAMPLE 50

A mixture of 398 g. (1 mol) of the bis-oxamidate ester of 4,4'-diamino-diphenylmethane and 400 g. (1 mol) of the bis-oxamidate of 4,4'-diaminodiphenyl ether is melted at 140° C for 2 hours with 500 g. of 4,4'-diisocyanato-diphenyl ether. After adding 0.1 g. of lithium phenolate the temperature is raised during 2 hours to 200° C and the mixture stirred for 6 hours more at 200°–210° C. After cooling to 170° C, 1500 g. of N-methylpyrrolidone are stirred in. A clear, yellow-red viscous solution is obtained. Yield: 2730 g.

EXAMPLE 51

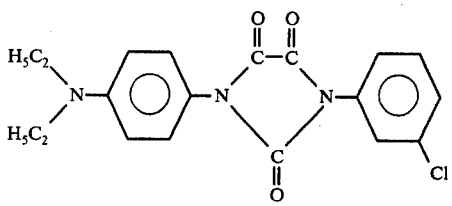

265 g. (1 mol) of ethyl(p-diethylaminophenyl)-oxamidate (melting point 73° C, light-yellow colored) are dissolved in 500 ml. of toluene and mixed at room temperature with 5 ml. of triethylamine.

310 g. (2 mol) of m-chlorophenylisocyanate are then added. The reaction is exothermic. To complete the reaction the reaction mixture is boiled under reflux for 6 hours. 350 ml. of toluene are then distilled off, the residue is diluted with 250 ml. of toluene, filtered with suction and washed with a ligroin-toluene (70:30) mixture. After drying in vacuo 260 g. of the above heavy orange-red colored compound are obtained.

Yield: 70% of theory, melting point 127°–128° C.

A sample recrystallised twice from cyclohexane-toluene yielded the following analysis

|   | found | calculated |
|---|-------|------------|
| N | 11.09 % | 11.30 % |
| Cl | 9.42 % | 9.56 % |

If the used oxamidate is substituted by either 1 mol of ethyl (p-diphenylaminophenyl)-oxamidate or of ethyl (p-ethyl-phenyl-aminophenyl)-oxamidate as a starting material the corresponding products are obtained.

EXAMPLE 52

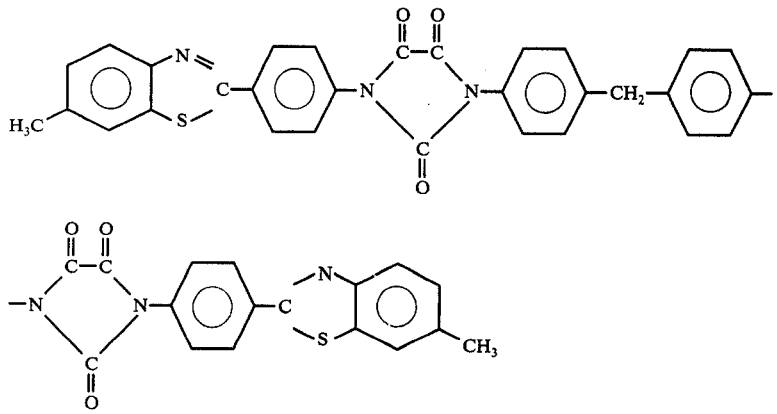

68 g of ethyl N-[4-(6-methyl-benzothiazolyl)-phenyl] oxamidate (0.2 mol) and 50 g of diphenylmethane diisocyanate (0.2 mol), 500 ml tolyene and 1 ml of triethylamine are boiled under reflux for 25 minutes. The paste of crystals formed is filtered with suction and washed with toluene. Yield: 147.5 g (88% of theory).

EXAMPLE 53

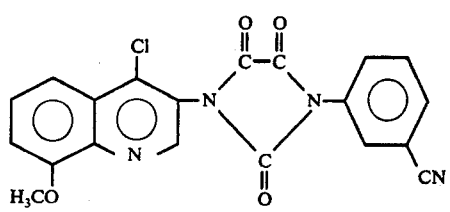

269 g of ethyl (8-methoxy-4-chloro-chinolyl)-3-oxamidate (1 mol) and 144 g of m-cyanophenylisocyanate (1 mol) are boiled under reflux for 5 hours at 150° to 155° C with 300 ml of chlorobenzene. After cooling the product crystallises out in pale yellow crystals which are filtered and washed with toluene. Yield: 310 g (= 84% of theory). The product is recrystallised from cyclohexanone/n-butanol.

EXAMPLE 54

384 g (1 mol) of 4,4'-di-ethoxalylaminodiphenyl, 197 g (1.17 mol) of 1,6-di-isocyanatohexane and 25 g (0.03 mol) of the isocyanate of formula XIII are kept for 1 hour at 150° C with 5 g of N-methylmorpholine and 0.5 g of iron acetylacetonate. 293 g of dimethylsulphoxide are then stirred in and stirring is continued for 4 further hours at 100° C.

A pale brown solution is obtained which may be applied to metal surfaces. After thermal treatment at 240° C a clear pale brown and elastic coating is obtained. It has — compared with the coating of example 39 — an essentially improved surface hardness and resistence to solvents.

What we claim is:

1. A process for the preparation of a monomer compound containing a structural unit of the formula

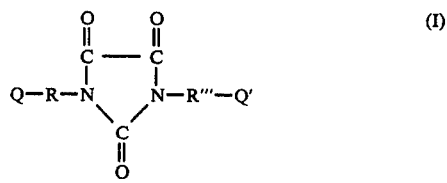

(I)

wherein one of Q and Q' are independently a urethane or an isocyanate group, the group NH—CO—OR$^{IV}$ or hydrogen and the other —NH—CO—COOR$^V$ or hydrogen, wherein R$^{IV}$ and R$^V$ are aliphatic hydrocarbon groups with up to 18 carbon atoms, cycloaliphatic hydrocarbon groups with up to 8 carbon atoms, mononuclear aromatic groups of 6 carbon atoms or such mononuclear aromatic groups of 6 carbon atoms substituted with hydrocarbon groups having up to 14 carbon atoms;

R is a radical selected from phenyl, naphthyl, benzeneazophenyl, anthraquinolyl, pyridyl, quinolyl, cycloaliphatic group that are unsubstituted or substituted with one or more groups selected from nitro, cyano, halo, lower alkyl, lower alkoxy, lower diethylamino alkyl ester, cycloalkyl, alkylsulphonyl and haloalkyl, R''' is a group as defined for R and additionally phenyl, naphthyl, phenylene, naphthylene, each of which can be substituted with alkyl, haloalkyl with up to 5 halogen atoms, trifluoromethyl, acyl such as acetyl or nitro groups comprising reacting at least one oxamidic acid ester as defined with a monoisocyanate or an isocyanate forming compound (A) at a temperature of −20° to 280° C at a molar ratio selected from the group consisting of
  (a) monoisocyanate to a monooxamidic ester being 1:1 to 2:1,
  (b) monoisocyanate to bis-oxamidic ester being 2:1,
  (c) diisocyanate to a monooxamidic ester being 1:1 and
(B) at a temperature of −20° to 150° C at a molar ratio of
  (d) diisocyanate to bis-oxamidic ester being 1:1 to 2:1 both embodiments (A) and (B) are performed in the presence or absence of a catalyst.

2. A process as claimed in claim 1 wherein the reaction is effected in the presence of an amine, phosphine, an alcoholate or an organic tin compound or of a mixture of a plurality of these compounds.

3. A process for the preparation of a monomer compound of the formula

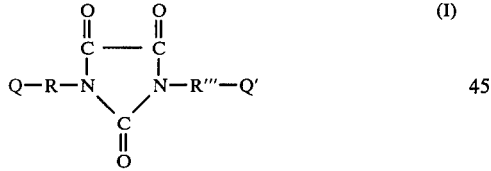

wherein R, R''', Q and Q' in formula (I) have the meaning as defined in claim 1 and wherein at least one oxamidic acid ester with the grouping —N-H—CO—CO—OR$^v$, wherein R$^v$ is as defined in claim 1, is reacted with an isocyanate or an isocyanate-forming compound at temperatures of −20° to +280° C in the presence or absence of a catalyst according to any of the following:

I. In preparing the compounds of formula I by reacting
  (a) a monoisocyanate with a monooxamidic ester in a molar ratio of 1:1 to 2:1,
  (b) a monoisocyanate with a bi-to tetravalent oxoamidic ester in a molar ratio of 1:1 to 8:1,
  (c) a diisocyanate with a monooxamidic ester in a molar ratio of 1:1,
  (d) a diisocyanate with a bi-to tetravalent oxamidic ester in a molar ratio of 1:1 to 4:1.

4. A compound of formula

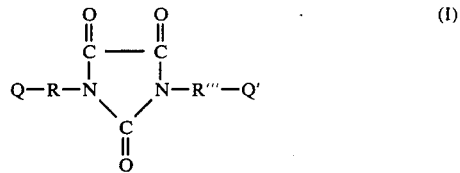

wherein one of Q and Q' are independently a urethane or an isocyanate group, the groups —NH—CO—OR$^{IV}$ or hydrogen and the other —NH—CO—COOR$^V$ or hydrogen, wherein R$^{IV}$ and R$^V$ are aliphatic hydrocarbon groups with up to 18 carbon atoms, cycloaliphatic hydrocarbon groups with up to 8 carbon atoms, mononuclear aromatic hydrocarbon groups with 6 carbon atoms or such mononuclear aromatic groups of 6 carbon atoms substituted with hydrocarbon groups having up to 14 carbon atoms;

R and R''' are independently an aromatic radical selected from phenyl, naphthyl, phenylene, naphthylene that are unsubstituted or substituted with nitro, halo, lower alkyl, lower alkoxy, or haloalkyl; and wherein the substitution in at least one aromatic group R and R''' by a halogen atom or an alkyl radical is present only
  (b1) in a compound having at least one substituent of the group alkoxy, and nitro or
  (b2) in a compound wherein R''' has the meaning as defined above, but is other than an unsubstituted phenyl group or monohalogen substituted phenyl group and wherein
  (c) in a compound wherein R is phenyl R''' has the meaning as defined above, but is other than an unsubstituted phenyl group.

* * * * *